US010758258B2

(12) United States Patent
Bazan Alvarez

(10) Patent No.: US 10,758,258 B2
(45) Date of Patent: Sep. 1, 2020

(54) CLAMP FOR MEDICAL USE

(71) Applicants: Antonio Bazan Alvarez, Navarra (ES); ANSABERE SURGICAL, S.L., Navarra (ES)

(72) Inventor: Antonio Bazan Alvarez, Navarra (ES)

(73) Assignees: Antonio Bazan Alvarez, Esquiroz, Navarra (ES); ANSABERE SURGICAL, S.L., Esquiroz, Navarra (ES)

( * ) Notice: Subject to any disclaimer, the term of this patent is extended or adjusted under 35 U.S.C. 154(b) by 24 days.

(21) Appl. No.: 16/301,072

(22) PCT Filed: May 12, 2017

(86) PCT No.: PCT/ES2017/070302
§ 371 (c)(1),
(2) Date: Nov. 13, 2018

(87) PCT Pub. No.: WO2017/194811
PCT Pub. Date: Nov. 16, 2017

(65) Prior Publication Data
US 2019/0209193 A1    Jul. 11, 2019

(30) Foreign Application Priority Data

May 12, 2016   (ES) ................. 201630607 U

(51) Int. Cl.
*A61B 17/30*  (2006.01)
*A61B 17/24*  (2006.01)
(Continued)

(52) U.S. Cl.
CPC .............. *A61B 17/30* (2013.01); *A61B 17/24* (2013.01); *A61F 2/186* (2013.01);
(Continued)

(58) Field of Classification Search
CPC ......... B25B 9/02; B25B 7/00; A45D 26/0066; A61B 17/30; A61B 17/24; A61B 17/0482;
(Continued)

(56) References Cited

U.S. PATENT DOCUMENTS 7,297,104 B2 * 11/2007 Vanden Hoek ...... A61B 17/062
128/898
8,092,478 B2 *  1/2012 Kotler ............... A61M 16/0666
606/191
(Continued)

FOREIGN PATENT DOCUMENTS

| CN | 104758026 A  | 7/2015 |
| CN | 201920804 U  | 6/2017 |
| CN | 104814776 U  | 8/2017 |

OTHER PUBLICATIONS

WIPO, International Search Report, dated Jun. 29, 2017, in International Application No. PCT/E32017/070302, filed May 12, 2017.
(Continued)

*Primary Examiner* — George J Ulsh
(74) *Attorney, Agent, or Firm* — Thedford I. Hitaffer; Hitaffer & Hitaffer, PLLC

(57) ABSTRACT

The invention relates to a clamp for medical use, particularly for use in aesthetic and reconstructive rhinoplasty procedures, said clamp comprising two arms (1) connected at corresponding ends, with a scoop (2) provided at the free end of each arm (1). Each scoop (2) comprises: on one longitudinal edge, a recess (3) with a plurality of through-holes (4), the size of which allows the double pass of a needle; and, on the longitudinal edge opposite the recess (4), respective opposing longitudinal projections (5).

5 Claims, 1 Drawing Sheet

(51) Int. Cl.
*A61F 2/18* (2006.01)
*A61B 17/122* (2006.01)
*A61B 17/28* (2006.01)
*A61B 17/04* (2006.01)

(52) U.S. Cl.
CPC ......... *A61B 17/0482* (2013.01); *A61B 17/122* (2013.01); *A61B 17/282* (2013.01); *A61B 17/2833* (2013.01); *A61F 2220/0008* (2013.01)

(58) Field of Classification Search
CPC . A61B 17/122; A61B 17/282; A61B 17/2833; A61F 2/186; A61F 2220/0008
See application file for complete search history.

(56) References Cited

U.S. PATENT DOCUMENTS

| | | | | |
|---|---|---|---|---|
| 9,393,143 | B1* | 7/2016 | Fogel | A61F 5/0086 |
| 2006/0190033 | A1* | 8/2006 | Molloy | A61B 17/282 |
| | | | | 606/205 |
| 2007/0197858 | A1* | 8/2007 | Goldfarb | A61B 17/29 |
| | | | | 600/37 |
| 2008/0312669 | A1 | 12/2008 | Vries et al. | |
| 2016/0081833 | A1* | 3/2016 | LeBlanc | A61B 17/0482 |
| | | | | 606/144 |

OTHER PUBLICATIONS

WIPO, Written Opinion, dated Jun. 29, 2017, in International Application No. PCT/ES2017/070302, filed May 12, 2017.

* cited by examiner

CLAMP FOR MEDICAL USE

CROSS-REFERENCE TO RELATED APPLICATIONS

This application, filed under 35 USC 371, is a United States National Stage Application of International Application No. PCT/ES2017/070302, filed May 12, 2017, which claims priority to ES Application No. U201630607, filed on May 12, 2016, the disclosures of which are incorporated herein by reference.

TECHNICAL SECTOR

The present invention relates to a clamp for medical use, particularly for use in aesthetic and reconstructive rhinoplasty procedures.

STATE OF THE ART

Rhinoplasty is a surgical procedure that modifies the shape of the nose, and is one of the surgical procedures most frequently performed in plastic surgery. It primarily solves aesthetic problems of the nose, such as a bone hump, deviations to the right or left of the entire nose, and congenital defects such as cleft lip and palate sequelae and other genetic factors. It also corrects congenital problems, traumas, and some respiratory problems.

In some aesthetic and reconstructive rhinoplasty procedures, a dorsal spreader graft must be coupled on at least one side of the nasal septum so that it can act as cartilage. These grafts consist of two thin layers or strips of cartilage (generally about 3 mm in width and 2.5 cm in length). When placement is performed by means of closed rhinoplasty, they are placed bilaterally in corresponding subperichondrial tunnels, right on the anterior border of the septum and surpassing the caudal border of the nasal bones, below the dome. Both the cranial and caudal ends must be fixed to one another through the border of the septum with resorbable sutures. Their mission is to separate the anterior border of the lateral cartilages from the septum, which causes an increase in the angle formed between them and, therefore, in the spreading open of the internal valve.

The same procedure is followed in open rhinoplasty, with the exception that instead of creating a tunnel on each side to fit the grafts in the pocket, the mucosal and perichondrial flap can be detached at the level of the anterior septum and under direct visualization, i.e., it facilitates the procedure by allowing greater control over positioning, a more precise fixation with non-resorbable sutures (which will prevent subsequent displacements of the grafts) and better modeling of the anterior border of the assembly formed by the grafts and the anterior septum. In other words, although spreader grafts can be used in both open and closed rhinoplasty, an assessment of their necessity may justify selecting the external approach (open rhinoplasty), unless the patient has very large nostrils which enable safely handling the fixation of said grafts.

In the technical field of surgery today, there is no knowledge of the use of an external tool for aiding in the placement of dorsal spreader grafts. Instead, these grafts are placed directly on both sides of the septum, being held only by a general instrument, such as clamps.

This earlier method with respect to the invention entails the following drawbacks:

Need for the assistance of more medical professionals.

Impossibility of aligning the two lateral grafts simultaneously.

Possibility of the grafts moving to an unwanted position when fixation to the septum is performed by means of suture.

Today, this entails holding the graft or grafts in place with a clamp, assuring with a hand the pressure needed so that it will not move from its site. However, it is a complicated task to position grafts precisely in the necessary location while maintaining pressure and performing an entire series of procedures, such as stitching the grafts to the septum. A displacement of the graft that goes undetected may cause lateral angulations or deviations in the reconstruction of the nose and an unsuitable rhinoplasty result.

The applicant has no knowledge of any clamp which offers the advantages of this invention.

BRIEF DESCRIPTION OF THE INVENTION

The invention consists of a clamp according to the claims. It solves with its various embodiments the problems of the state of the art.

Use of the invention provides the following advantages:
  It facilitates the correct positioning of dorsal spreader grafts in aesthetic and reconstructive rhinoplasty.
  It enables the correct alignment of the nasal axis and the correction of lateral angulations.
  It improves graft placement time.
  It facilitates the suturing of the grafts to the septum as a result of the grafts being held.
  It prevents the need for a surgeon to intervene to hold the grafts.

The clamp for medical use is of the type comprising two arms connected at corresponding ends, and its novelty lies in comprising a scoop or basket at the free end of each arm. Each scoop comprises: on one longitudinal edge (parallel to the direction of the arm), a recess with a plurality of eyelets or through-holes, the size of which allows the double pass of a needle. On the longitudinal edge opposite the recess, respective opposing longitudinal projections are defined by the mere absence of a recess.

To free up the operating space for the surgeon, the arms preferably have a bent shape, with the bend located on the side of the projections. Therefore, the clamp could be held from a lower position, which would prevent interfering with the rest of the procedures performed by the surgeon.

In order to assure that pressure is homogeneous and there is no slippage, the clamp may comprise a fastener to keep the arms connected in the closed position. For example, this fastener could be a pin connected to one of the arms and going through the other one, such that a nut or knob threaded at its free end allows tightening or releasing the clamp.

It is possible to arrange on the internal surface of each recess at least one protrusion which locks onto the graft. The risk of slippage is thereby even further reduced.

As a result, the different variants of the invention offer a series of features making it very advantageous:
  Design for the placement of the 2 grafts simultaneously.
  Optimal holding of the grafts along the entire length of said grafts.
  Protrusions in the baskets of the clamps where the grafts are housed so that they are maintained in the desired position.
  Lateral holes which allow suturing and fixation to the septum.
  Complete control over opening and stabilization by means of a threaded knob.

Design of tips so that it is not traumatic for the patient
Design of the clamp in bayonet form and with an ergonomic design.

DESCRIPTION OF THE DRAWINGS

To better understand the invention, the following figures are included.

EMBODIMENTS OF THE INVENTION

An embodiment of the invention is very briefly described below as an illustrative and non-limiting example thereof.

The clamp of the invention comprises two arms (1) which are approximately parallel and connected at corresponding ends, similar to any clamp.

The clamp comprises, however, a series of modifications which offer advantages in its use in rhinoplasty procedures.

First, the free ends of the clamp comprise two baskets or scoops (2), which correspond to wider portions. These measurements may vary according to the patient.

Figure 1:
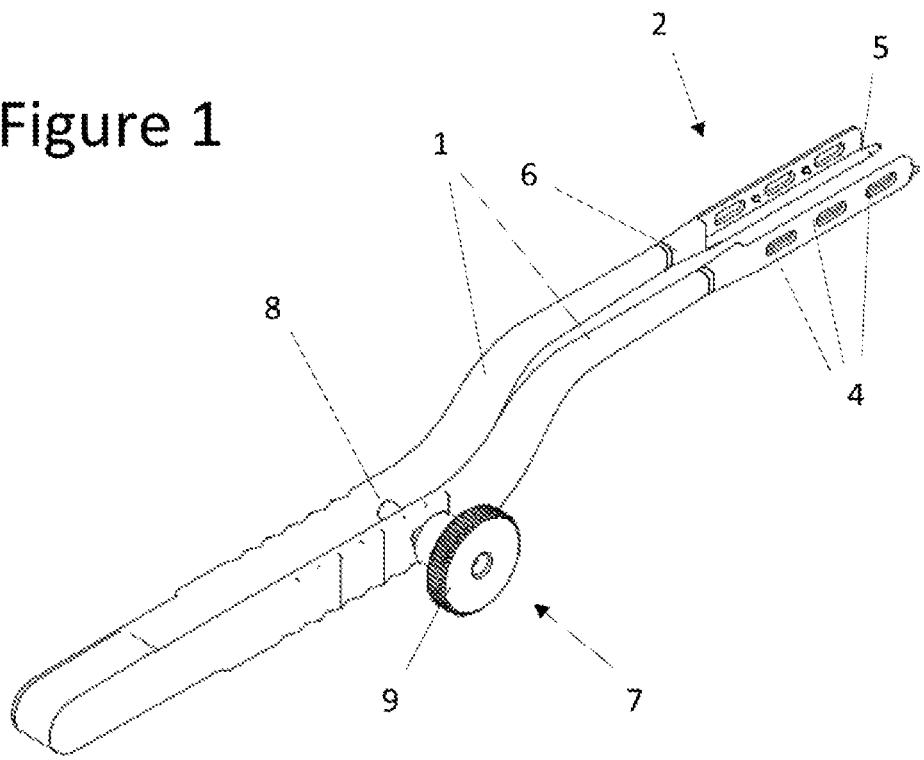
FIG. 1: a perspective view of an exemplary embodiment of the invention.
Figure 2:
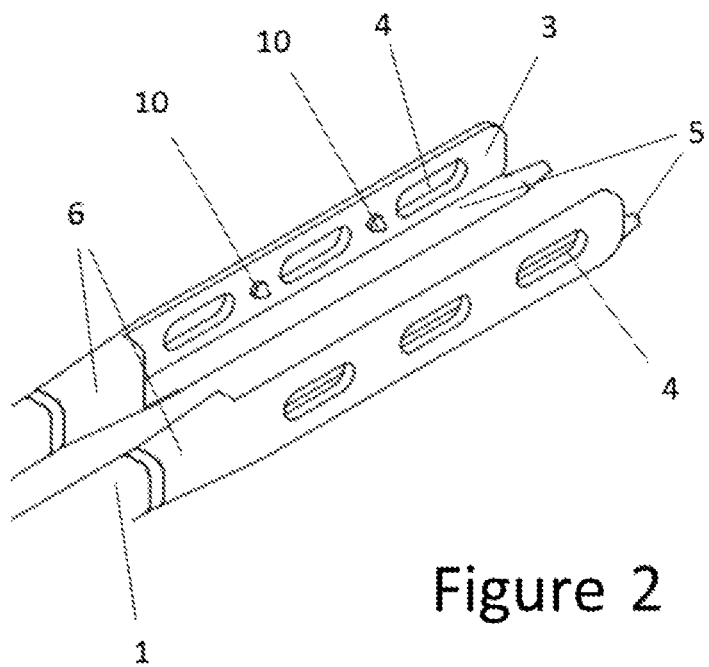
FIG. 2: a detail view of the scoops of the embodiment of FIG. 1.

As can be seen in FIG. 1, the scoops (2) are approximately symmetrical. Each scoop (2) has, on a longitudinal edge of its free end, a recess (3) forming a planar area away from the area of contact between the arms (1). A plurality of through-holes (4) are made in these recesses (3). No recess is made on the opposite longitudinal edge of each scoop (2), so a longitudinal projection (5) directed towards the opposite scoop (2) which may be somewhat longer than the area with the recess (3), is formed. Therefore, when the clamp is closed, the recesses (3) are spaced apart but the projections (5) do come into contact with one another. The difference in length between the projections (5) and the rest of the scoop (2) or basket reduces the trauma or pain caused for the patient when the clamp is moved forward and the previously created tunnel is expanded without the mucosa tearing, particularly when the projections (5) are finished with a blunt tip: a rounded or "bullet" tip. In any case, it is difficult to avoid scratching or injuring the pericardium and/or mucosa with the "fitting" or placement movements, so it is favorable to define the tip of the projection (5) so as to prevent these injuries.

The nexus between the scoops (2) and the rest of the arms (1) is a base (6) the width of which is preferably equal to the wide of the longitudinal projection (5) to assure the complete support of one arm (1) on the opposite one when closing the clamp.

Preferably, the arms (1) have a bent shape, with the longitudinal projection (5) located in the inner part of the bend, i.e., on the edge of the scoop (2) closest to the change in direction.

To facilitate use and enable keeping the graft in place, tightened against the nasal septum, the arms (1) will preferably comprise a tightening fastener (7) which allows keeping the clamp closed with the desired pressure. The preferred form is a threaded pin (8) connected to one arm (1) and going through the opposite arm (1). A tightening nut (9) or knob is arranged at the free end of the pin (8).

One or more protrusions (10), preferably at least two, which secure the grafts in place while suturing is performed, could be arranged on the surface of each recess (3). For example, those protrusions (10) may be small locking tips. Another option is a series of teeth on the entire or on part of the surface of the recesses (3).

During use, the physician uses the clamp to hold the graft or set of grafts connected to the nasal septum in place. The nasal septum is clamped by the projections (5), the upper surface of which serves as a support and a stop for a graft, and they can be clamped by the recesses (3). The clamp thereby allows placing the grafts and keeping them in the desired position with one hand. Furthermore, the fastener (7) allows assuring that they do not move without having to make an effort with the hands. On the other hand, the stitching of the graft or grafts by means of a needle and thread is allowed as a result of the holes (4). Specifically, the user will pass the needle through the holes (4), the dimension of which will be sufficient so that the needle can pass therethrough on its path twice (out and in) for each stitch, with sufficient spacing so as not to sew the clamp to the septum. An example of holes (4) would be ovals with a major axis of 4 mm in length.

The invention claimed is:

1. A clamp for medical use, the clamp comprising: two arms with respective proximal and free distal ends, the two arms are connected at corresponding proximal ends, the two arms further comprising a scoop at the free distal end of each arm, and wherein each scoop comprises: a longitudinal edge, wherein the longitudinal edge further comprises a recess with a plurality of through-holes, wherein said plurality of through-holes are configured to allows a double pass of a needle, and wherein an internal surface of each recess has one or more protrusions; and, wherein each scoop comprises an opposite longitudinal edge opposite the recess, the opposite longitudinal edge further comprises respective opposing longitudinal projections, wherein the longitudinal projections extend from a distal end of each scoop, and the longitudinal projections are longer than a remainder of each scoop.

2. The clamp according to claim 1, wherein the two arms have a bent shape creating a bend, wherein the bend is located on a side of the projections.

3. The clamp according to claim 1, comprising a fastener to keep the two arms connected in the closed position.

4. The clamp according to claim 3, wherein the fastener comprises a pin connected to one arm and going through the opposite arm, with a nut at a free end of the pin.

5. The clamp according to claim 1, wherein the projections are finished with rounded tips.

* * * * *